United States Patent
Lockhart

(10) Patent No.: US 6,974,673 B2
(45) Date of Patent: Dec. 13, 2005

(54) COUPLED CAPILLARY FIBER BASED WAVEGUIDE BIOSENSOR

(75) Inventor: Michael D. Lockhart, Charlottesville, VA (US)

(73) Assignee: Veridian Systems Division, Charlottesville, VA (US)

( * ) Notice: Subject to any disclaimer, the term of this patent is extended or adjusted under 35 U.S.C. 154(b) by 374 days.

(21) Appl. No.: 09/961,464

(22) Filed: Sep. 24, 2001

(65) Prior Publication Data

US 2003/0059853 A1 Mar. 27, 2003

(51) Int. Cl.$^7$ .............................................. G01N 21/64
(52) U.S. Cl. ...................... 435/7; 250/458.1; 422/57; 422/58; 422/59; 422/68; 435/288; 435/291; 436/518; 436/524; 436/528; 356/317
(58) Field of Search ................................ 436/527–535, 436/800–808, 518, 524; 422/55–61, 82.06, 82.1, 68; 356/317; 385/24, 37; 378/119, 145; 250/458.1; 435/288, 291, 7

(56) References Cited

U.S. PATENT DOCUMENTS 4,122,342 A  * 10/1978 Vali et al. ...................... 378/70
4,447,546 A  * 5/1984 Hirschfeld ................... 436/527

(Continued)

OTHER PUBLICATIONS

Renn et al, Evanescent–wave guiding of atoms in hollow optical fibers, 1996, Phys Rev A, 53(2), R648–R651.*

*Primary Examiner*—Long V. Le
*Assistant Examiner*—Nelson Yang

(74) *Attorney, Agent, or Firm*—Gifford, Krass, Groh, Sprinkle, Anderson & Citkowski, PC

(57) ABSTRACT

An evanescent-wave optical biosensor includes a hollow optical waveguide, preferably in the form of a light-conductive capillary, surrounding a central waveguide preferably in the form of an optical fiber to create a sealed cavity. A source of optical energy as from a laser is directed into one or both of the light-input ends of the capillary and fiber, such that an evanescent field extends into the cavity from one or both of the inner surface of the capillary and the outer surface of the fiber. A first biomolecular constituent is attached to one or both of the inner wall of the hollow optical waveguide and the outer surface of the second optical waveguide, such that the first biomolecular binding partner is substantially within the evanescent field if present. A first optoelectric detector is supported to receive light from the light-output end of the capillary and convert the light received into a first electrical signal, and a second optoelectric detector is supported to receive light from the light-output end of the fiber and convert the light received into a second electrical signal. A fluid within the cavity which may contain a second biomolecular constituent having a binding affinity to the first biomolecular constituent, such that if binding occurs between the biomolecular constituents, a representative change occurs in the light emerging from one or both of the output ends of the hollow and second optical waveguides and the electrical signals from the optoelectric detectors.

17 Claims, 6 Drawing Sheets

U.S. PATENT DOCUMENTS

| | | | |
|---|---|---|---|
| 4,558,014 A * | 12/1985 | Hirschfeld et al. | 436/527 |
| 4,654,532 A * | 3/1987 | Hirschfeld | 250/458.1 |
| 4,671,938 A * | 6/1987 | Cook | 422/57 |
| 4,834,496 A * | 5/1989 | Blyler et al. | 385/12 |
| 4,846,548 A | 7/1989 | Klainer | 350/96.29 |
| 4,852,967 A | 8/1989 | Cook et al. | 350/96.29 |
| 4,880,752 A * | 11/1989 | Keck et al. | 435/7.72 |
| 4,909,990 A * | 3/1990 | Block et al. | 422/82.11 |
| 4,980,278 A | 12/1990 | Yamada et al. | 435/7 |
| 5,173,747 A | 12/1992 | Boiarski et al. | 356/361 |
| 5,227,134 A | 7/1993 | Janata | 422/82.08 |
| 5,340,715 A | 8/1994 | Slovacek et al. | 435/6 |
| 5,377,008 A | 12/1994 | Ridgway et al. | 356/361 |
| 5,416,879 A | 5/1995 | Liu | 385/125 |
| 5,494,798 A | 2/1996 | Gerdt et al. | 435/6 |
| 5,512,492 A | 4/1996 | Herron et al. | 436/518 |
| 5,525,466 A | 6/1996 | Slovacek et al. | 435/6 |
| 5,631,170 A | 5/1997 | Attridge | 436/518 |
| 5,639,668 A | 6/1997 | Neel et al. | 436/172 |
| 5,738,992 A | 4/1998 | Cook et al. | 435/6 |
| 5,841,914 A | 11/1998 | Shieh et al. | 385/12 |
| 5,846,842 A | 12/1998 | Herron et al. | 436/518 |
| 5,864,641 A | 1/1999 | Murphy et al. | 385/12 |
| 6,021,240 A | 2/2000 | Murphy et al. | 385/37 |
| 6,188,812 B1 | 2/2001 | Kao et al. | 385/12 |
| 6,445,861 B1 * | 9/2002 | Shaw et al. | 385/123 |

* cited by examiner

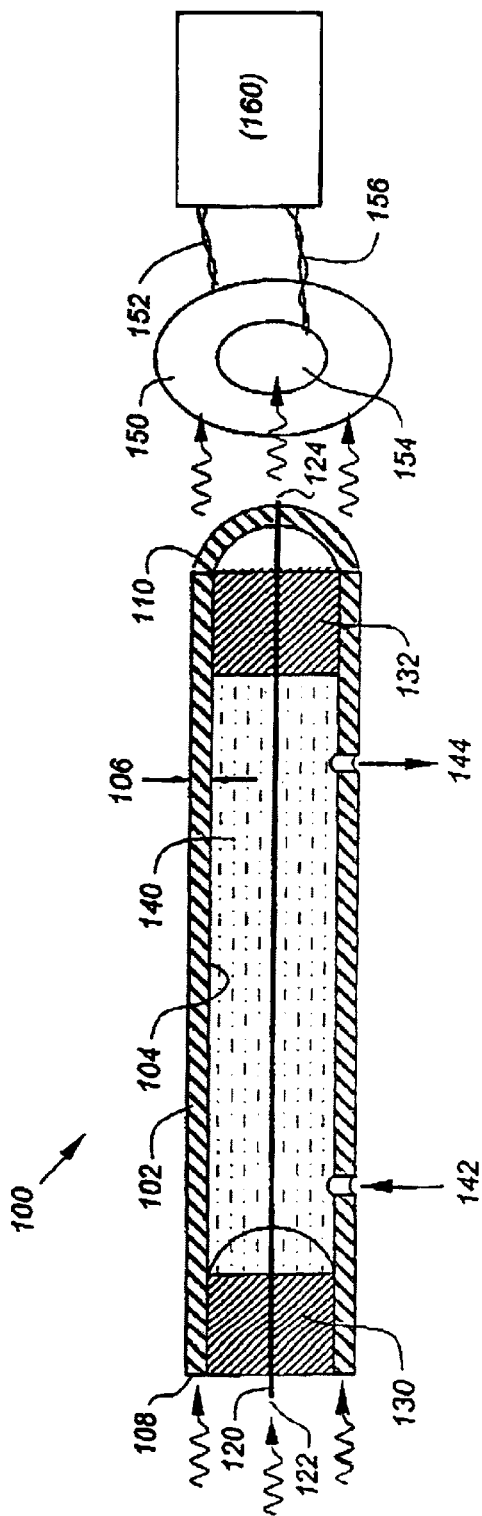
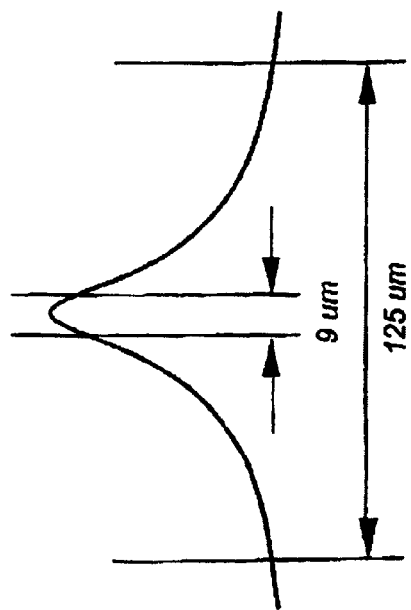

COUPLED CAPILLARY FIBER BASED WAVEGUIDE BIOSENSOR

FIELD OF THE INVENTION

This invention relates generally to waveguided biosensors and, in particular, to a sensor that utilizes a parallel optical fiber/capillary combination to achieve a sensor configuration with enhanced capabilities.

BACKGROUND OF THE INVENTION

Optical fibers are being used in a variety of biosensor applications. For example, as discussed in U.S. Pat. No. 5,494,798, a fused biconical fiber optic fiber coupler may be used without cladding to exploit the evanescent field present immediately outside the fiber/air interface in its "waist" region. If an antibody is bound to the exposed surface of the bare waist region of the fiber optic coupler, the evanescent field envelopes the molecule. But since there is little or no absorption or other phenomena to alter the amount of the light carried by the fiber, no attenuation or detectable characteristics are developed.

However, when the antibody's target antigen binds to the antibody, the localized changes in refractive index in the evanescent field cause characteristic changes in the ratio output of the fiber optic coupler.

Whereas previous fiber-optic evanescent-wave sensors utilized multi-mode fibers and are primarily based on fluorescence, the '798 patent improved on the technique by employing a pair of single-mode optical fibers in a coupler arrangement measuring changes in refractive index. Light is introduced into one of the fibers to produce an evanescent region surrounding the coupling area, and the magnitude of light emitted from the pair of fibers is compared for detection purposes.

Light from a laser diode is inserted into a first leg of the fiber optic coupler, and exits from the same fiber, forming an input channel. The second fiber of the coupler provides an output channel for light from the first leg. A first photo diode detector is connected to the input channel and a second photo diode detector is connected to the output channel. Each detector feeds its own transimpedance amplifier, the outputs of which are applied to A/D converters providing digital electrical signals to an instrumentation board and attached personal computer which outputs results to a printer and monitor.

The finished probe includes the fiber optic coupler and attached antibodies, which yields a baseline ratio for the sensor. The finished probe is then exposed to a material of interest, and the ratio of the light through the two sides of the coupler changes as a function of the way in which the target attaches. That is, the localized index of refraction at the coupling region and the determination of the ratio is a function of the binding of the molecular target to the bound receptor in the coupler region.

Though versatile for some applications, the apparatus just described is limited in terms of applicable optical characteristics as well as amenability to large-scale production. Difficulties in construction lead to poor, irreproducible operational characteristics. This in turn minimizes the applicability for using polarization, interference and other potentially useful optical phenomena in favor of a strict magnitude comparison. Thus, the need remains for a more versatile arrangement utilizing evanescent field detection which affords greater sensitivity while being conducive to larger-scale production at low cost.

SUMMARY OF THE INVENTION

This invention improves upon the existing art by providing an optical biosensor wherein a pair of single mode optical waveguides are positioned with respect to each other such that evanescent light from a first waveguide is transmitted via a second waveguide.

In a preferred embodiment, a hollow optical waveguide surrounds a central waveguide to create a cavity containing biomolecular constituents to be investigated. Preferably, the hollow waveguide is a glass capillary and the second waveguide is an optical fiber.

The capillary has a light-input end, a light-output end, and a wall with a thickness and an inner surface. The optical fiber having a light-input end, a light-output end, and a length with an outer surface disposed within the capillary. Ferrules are preferably used at both ends of the waveguides for bonding and centering purposes, thereby creating a sealed cavity between the inner surface of the capillary and the outer surface of the fiber.

A source of optical energy as from a laser diode is directed into one or both of the light-input ends of the capillary and fiber, such that an evanescent field extends into the cavity from one or both of the inner surface of the capillary and the outer surface of the fiber. A first optoelectric detector is supported to receive light from the light-output end of the capillary and convert the light received into a first electrical signal, and a second optoelectric detector is supported to receive light from the light-output end of the fiber and convert the light received into a second electrical signal.

A first biomolecular constituent is attached to one or both of the inner wall of the hollow optical waveguide and the outer surface of the second optical waveguide, such that the first biomolecular binding partner is substantially within the evanescent field if present. A fluid within the cavity which may contain a second biomolecular constituent having a binding affinity to the first biomolecular constituent, such that if interaction occurs between the biomolecular constituents, a representative change occurs in the light emerging from one or both of the output ends of the hollow and second optical waveguides and the electrical signals from the optoelectric detectors.

An advantage of the arrangement is that in addition to light intensity or magnitude comparisons, the light conducted by one or both of the capillary and optical fiber may assume different optical polarities, enabling at least the second optical detector to sense a change in the optical polarity for analysis purposes. In the preferred embodiment the light traveling through the fiber and capillary are single mode. This minimizes optical modal interferences. In addition, the light conducted by the capillary is many applications is able to propagate in multiple optical modes, with the presence/absence of the constituent binding event still being determinative of the changes of localized refractive index within the evanescent field.

In the preferred physical implementation, the second optoelectric detector includes an aperture through which the optical fiber protrudes to minimize interference between the energy received by the first and second optoelectric detectors. A plurality of sealed waveguides may also be used, each having a cavity in common fluid communication.

In a further preferred embodiment, the first and second waveguides are positioned in parallel and next to each other such that the second waveguide is within the evanescent field of the first waveguide at a region along its length. The first and second waveguides each have a light-input end, a light-output end, and a length with an outer surface and a wave-propagating interior. A source of optical energy as from a laser diode is directed into one or both of the light-input ends of the first and second waveguides, such that an evanescent field emanates from one or both of the outer surfaces of the waveguides into the interior of the other. A first optoelectric detector is supported to receive light from the light-output end of the first waveguide and convert the light received into a first electrical signal, and a second optoelectric detector is supported to receive light from the light-output end of the second waveguide and convert the light received into a second electrical signal.

A first molecular constituent is attached to the first or second waveguide, or both, at least in the region where the second waveguide is within the evanescent field of the first waveguide. A test sample which may contain a second molecular constituent is brought into proximity with a waveguide having the attached first molecular constituent. In a preferred embodiment, a region of the pair of waveguides having an attached molecular constituent is situated in a sample container.

Any single mode waveguide which allows emanation of an evanescent field is operative in the optical sensor of the present invention. In a preferred embodiment, two optical fibers are used as waveguides. In a further preferred embodiment, two planar waveguides are used.

The invention is not limited in terms of sample type, and may be adapted to sense or investigate at least the following types of interactions: antigen-antibody, carbohydrate-lectin, receptor-ligand, receptor-toxin, substrate-enzyme, effector-enzyme, inhibitor-enzyme, complimentary nucleic acid strands, binding protein-vitamin, binding protein-nucleic acid, reactive dye-protein, and reactive dye-nucleic acid interactions.

BRIEF DESCRIPTION OF THE DRAWINGS

FIG. 1 is a drawing which provides an overview of apparatus according to the invention;

FIG. 2 illustrates dimensions associated with capillary wall and an optical wave propagating along the wall;

DETAILED DESCRIPTION OF THE INVENTION

Figure 3:
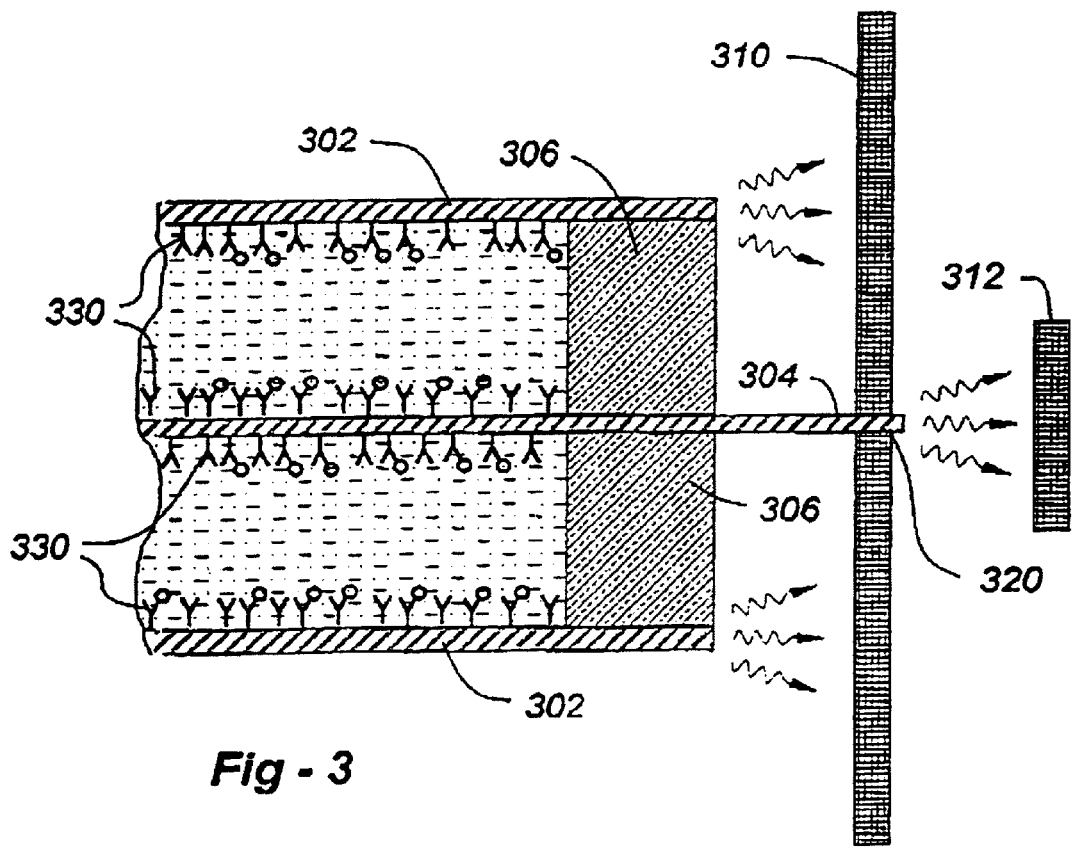
FIG. 3 is a drawing which shows a portion of a preferred embodiment of the invention.

Reference is now made to FIG. 1, which is a drawing used to illustrate important structures and functional operation according to the invention. The basic configuration, shown generally at 100, includes an optically conductive hollow waveguide 102 and a second waveguide 120 supported therewithin. The hollow waveguide 102 has a light-input end 108, and a light-output end 110, and a wall having a thickness 106 and an inner surface 104. Likewise, the second waveguide 120, features a light-input end 122, a light-output end 124, and an outer surface generally facing the inner surface 104 of the hollow waveguide 102.

In the preferred embodiment, the hollow waveguide 102 is a glass capillary, and the second waveguide 120 is an optical fiber. Conveniently, the waveguide 120 may be held in position using ferrules 130 and 132 which seal against the inner wall 104 of the waveguide 102, and have central apertures through which the waveguide 120 may be threaded. Preferably, the waveguide 120 is cemented in a taunt position centrally within the hollow waveguide 102, though precise registration is not absolutely necessary according to the invention.

By bonding the waveguides to ferrules 130 and 122, a cavity 140 is created, enabling a fluid containing a target substance to enter into the cavity through port 142, and exit from the cavity through a port 144, and thereby creating a flow cell.

According to the invention, light from a source such as a laser (not shown) is introduced into either or both of the light-input ends (108, 122) of the hollow waveguide 102 and second waveguide 120. Preferably, light is introduced at least into the central waveguide, and if light is introduced into both waveguides, the light may have different characteristics, such as wavelength, polarization and modes of propagation, as discussed below.

Opto-electric detectors 150 and 154 are supported to receive light emanating from the light-output ends (110, 124) of the hollow waveguide 102 and second waveguide 120. These opto-electric detectors, in turn, develop electrical signals representative of the light received, for communication to analytical equipment 160 through respective electrical paths 150, 156. The hollow waveguide 102 is a glass capillary, and the second waveguide 120 is an optical fiber. The thickness 106 of the wall of the waveguide 102, and the diameter of the waveguide 120, are such that when optical energy is carried there through evanescent fields are present. These fields extend at least from the inner wall 104 and outer surface of the waveguide 120 into the cavity 140. As discussed in further detail below, biomolecular constituents are attached to one or both of the inner surface 104 of the hollow waveguide and the outer surface of the second waveguide 120, such that if and when biomolecular constituents are present in the fluid within cavity 140 bind to the constituents on the surfaces of the waveguides, a change occurs in the light propagating through the waveguide(s), enabling detectors 150 and 154 to monitor such changes for delivery to equipment 160. The circuitry, or variants of the circuitry described in U.S. Pat. No. 5,494,798, the entire contents of this reference being incorporated herein.

Capillaries suitable to the invention are commercially available from a number of sources, including Chemglass, Vitronix, and Nissan Electric Glass. Such capillaries are manufactured for a different purpose, namely, gas and liquid chromatography and such tend to have an outer diameter of 1 mm or smaller, and wall thicknesses in the range of 50–200 microns. Such devices are fabricated entirely of quartz or fused silica. An effective capillary waveguide can be made by coating a low refractive index polymer capillary with sol-gel coatings. A sol-gel is a poly-silicone dioxide made from silicone oxide monomers, coated and then fixed (heat treatment) in situ. Often referred to as smart materials, these coatings can be made to many specifications of thickness and physical properties like hydrophobicity, hydrophilicity, etc. They can be readily doped so that accurate control of refractive index is possible.

Optical fibers applicable to the invention are preferably buffer-free; that is, the outer plastic or polymeric buffer of the fiber is stripped off leaving the core surrounded by the cladding. The cladding is on the order of 125 microns, but the core is only about 9 microns for communications-grade fibers, enabling optical energy propagating along the fiber to expose its evanescent field around the outer surface of the fiber, as shown in FIG. 2. FIG. 2 illustrates how a single-mode type 9/125 fiber allows very little power to extend outwardly from the cladding, while facilitating a much larger degree of evanescent field outside the 9 micron core. It will be noted that the invention is not limited to a second or central waveguide which is buffer-free, since it is also possible to stretch or pull fibers down to appropriate diameters with cladding or with an effective cladding of the surrounding buffer solution, and such material would be useful as well. Operations such as etching may also be used to strip the cladding off of an available fiber and or capillary, thereby leaving the core, which would also result in a second or central waveguide suitable to the invention.

FIG. 3 is a drawing which shows a preferred embodiment of the invention, showing the way in which the opto-electric detectors are supported to receive light from the waveguides. The overall length of the assembly is typically on the order of an inch or more, but in contrast to gas chromatographs or other instruments, excess lengths are not necessary for acceptable performance levels. It is an important aspect of the invention that the light exiting from the light-output ends of the waveguides are detected accurately and independently, since it is the relative characteristics or changes in the optical properties that enable the invention to precisely measure the presence and absence in biomolecular targets. A preferred arrangement for achieving acceptable results is depicted in FIG. 3. The capillary is shown at 302, and the centered fiber shown at 304, with both being bonded and sealed to ferrule 306. Light emerging from the capillary 302 is received by a first detector 310. To ensure that light from the fiber 304 is independently gathered, a second detector 312 is used, with an aperture 320 being formed through the first detector 310 through which the fiber 304 is threaded. Note that this, in common with the other drawings appended hereto, is not necessarily drawn to scale, such that the spaced-apart relationships shown in FIG. 3 may vary. For example, the detectors may be much closer to the respective waveguides, or, if sufficiently spaced-apart, focusing optics may be used between the light-output ends and detector surfaces.

Although detector 310 may be implemented with a custom device, there does exist commercially available detectors used in conjunction with lasers for optical centering purposes, and such existing devices may be used to sense the light exiting from the capillary 302. Such devices are typically provided in the form of an annulus divided into four quadrants, in which case the signals developed through each quadrant may be processed to attain the goals of the embodiments described herein. For example, if a device with separately addressable quadrants or other regions, such a feature may be used to advantage to detect light from different sections of the capillary independently in terms of magnitude, polarization, modes of propagation, and so forth. Detector 312 may be implemented with one of a variety of discrete opto-electric detectors available from numerous suppliers.

In the event that the wavelengths of interest are in a visible region of the spectrum, silicon detectors may be used, whereas, other types of detectors such as compound-semiconductor detectors may be used if the light is in the infrared or other portions of the spectrum. In the infrared, for example, indium gallium arsenide detectors or detector arrays may be purchased from Hamamatsu Corporation. In any case, to increase accuracy/resolution, light received by either detector may be integrated over time to implement an effective photon counting arrangement.

Figure 4:
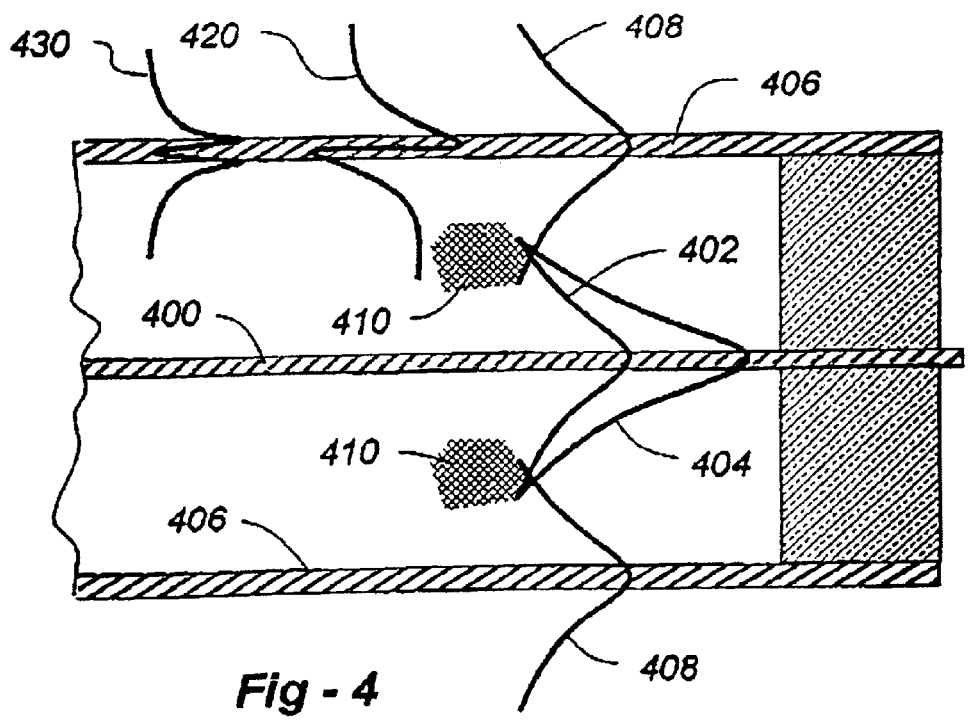
FIG. 4 is a drawing which shows a portion of a capillary and a portion of a fiber therewithin along with biomolecular constituents disposed within evanescent fields capable of altering index of refraction or other properties according to the invention.

The use of a hollow waveguide such as a capillary having a wall of a predetermined thickness offers the advantage that different optical modes of propagation may be supported and advantageously used to enhance detection. Making reference to FIG. 4, the distribution of the optical energy carried by a particular waveguide is a function of the shape of the guide, refractive index, and other factors. In FIG. 4, the shape of the energy distribution carried by the fiber 400 may assume a flattened shape 402 for a given refractive index, but may change to a narrower curve of the type shown at 404 due to changes in refractive index associated with the presence/absence of molecular constituents depicted in FIG. 3 as 330. The basic shape of the energy distribution may assume a conical or Bessel function or may be Gaussian in accordance with a physical characteristic such as core size, core-to-cladding ratio, capillary thickness, and so forth. The distribution of the optical energy down the wall of the hollow waveguide or capillary 406 in FIG. 4, is generally Gaussian if a single mode is present, but in contrast to optical fibers, hollow waveguides such as capillaries, unless they are coated waveguides are thick and subsequently are capable of propagating multiple optical modes, as shown by curves 420 and 430. These are simplified drawings of low-order modes, and it will be appreciated by those of skill that many more wave forms may be used to represent higher-modes of propagation.

Regardless of the modes, it will be noted that the interaction between optical energy present in the central waveguide interacts with, and may induce optical energy in the hollow waveguide, or change selective modes differently. The overlap between the energy carried by the two waveguides is depicted as areas 410. Note that as the shape of the curves change from 408 to 420 and 430, representative of different modes, the region of overlap changes as well, and these changes in interaction are detectable in accordance with the invention and, in fact, lead to very high resolution measurements which take into account secondary affects beyond mere magnitude as relied upon by existing devices. That is, depending upon the presence/absence of binding partners on the inner wall of the hollow waveguide and/or second or central waveguide, differences in magnitude, propagational mode, and other characteristics are modified or induced, all of which may then be detected, either as absolute values or changes in ratio.

Figure 5:
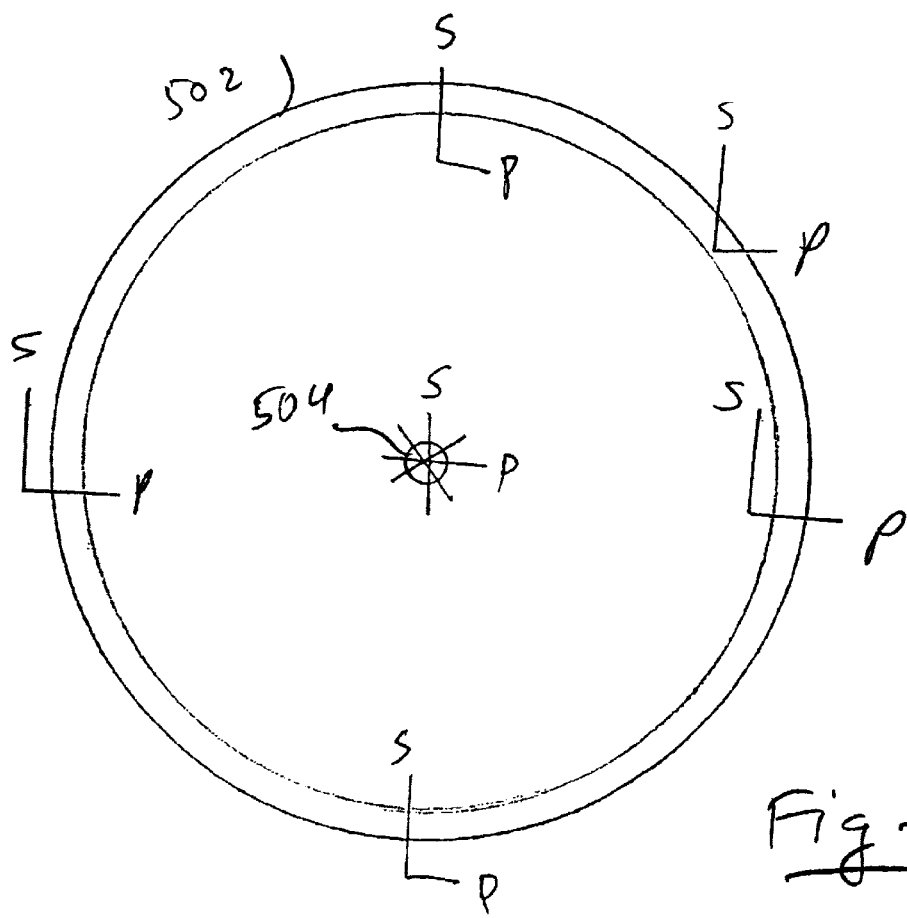
FIG. 5 is a cross-section of a capillary and central fiber used to illustrate states of polarization.

Moreover, particularly due to the inventive use of a hollow waveguide, changes in polarization may be readily detected as well, as shown schematically in FIG. 5. At the center, waveguide 504 carries optical energy having orthogonal S- or P-type polarizations. Whereas, with the hollow waveguide 502, the coupling of light into this planar waveguide from a fiber is at its maximum when the light is perpendicular to the tangent of the wall. Light traveling through the fiber in either the directions of S or P polarization states will induce greater coupling of that light in the capillary in the same relative S or P directions. Again, these changes in polarization may be modified or induced in accordance with the presence/absence of many molecular constituents which induce optical rotation as a function of binding to one or both of the surfaces of the hollow and central waveguide, and such changes are detectable according to the invention, not only in terms of magnitude, but also in terms of spatial orientation, particularly if two-dimensional opto-electric detectors are used.

Figure 6:
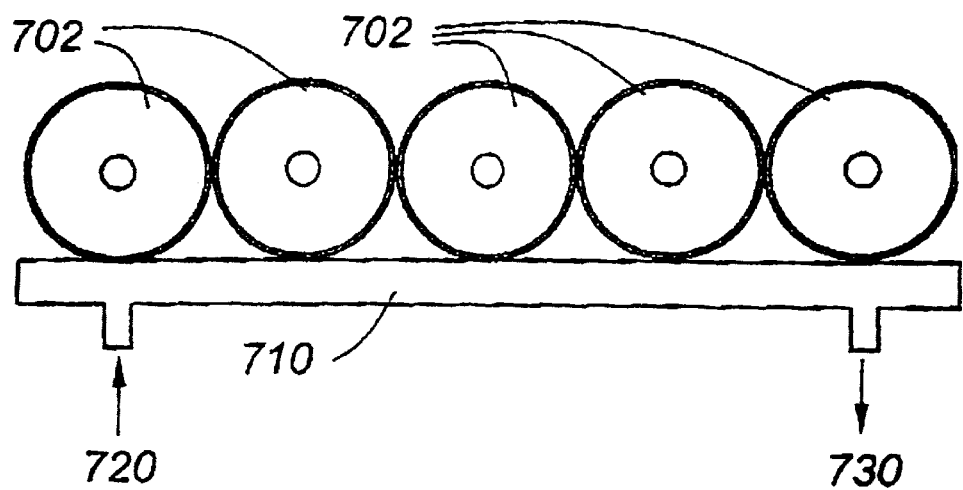
FIG. 6 is a drawing which shows how multiple flow cells according to the invention may be used to enhance throughput and/or functionality.

FIG. 6 is a drawing which shows how multiple flow cells according to the invention may be used in combination to detect different species, or to increase the resolution of detection of a single target. More particularly, flow cells 702 may be interconnected to a plenum 710, enabling the fluid containing a target constituent to enter into the system at 720 and exit therefrom at 730, having flowed through one or more of the cell structures.

Figure 7A:
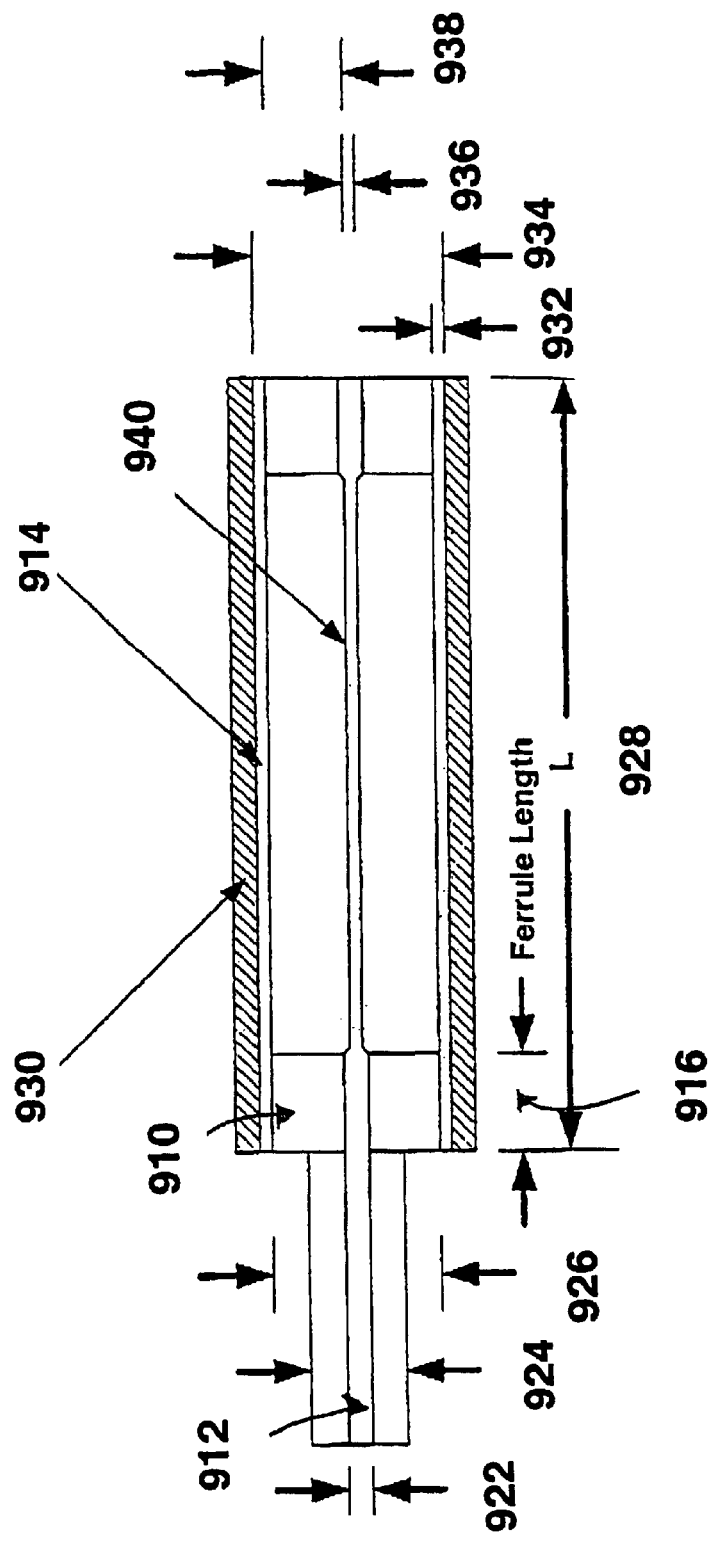
FIG. 7A is a drawing which shows a portion of a capillary and a portion of a fiber therewithin.
Figure 7B:
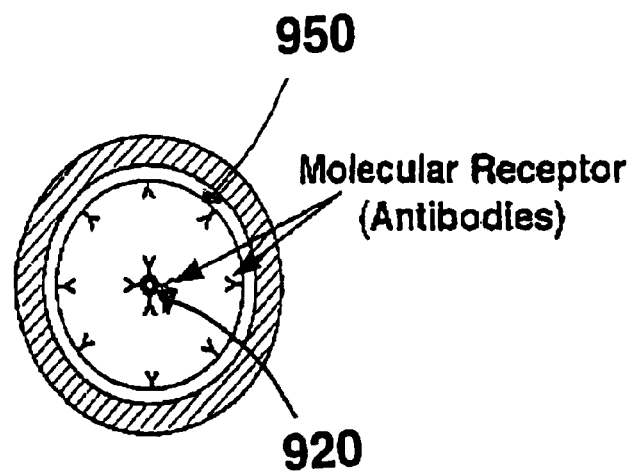
FIG. 7B is a drawing which shows a cross section of a capillary wherein a molecular receptor is localized on the capillary and a central fiber.

FIG. 7A is a drawing which shows a portion of a capillary and a portion of a fiber positioned within the capillary. In particular the drawing illustrates an arrangement of the biosensor wherein the fiber 912 is positioned within the capillary 914 using a ferrule 910. Ferrule length 916 may vary according to the application. A low refractive index isolator 930 is illustrated on the outer wall of the capillary. The drawing illustrates the reduced fiber diameter 940 along a region of the length of the fiber. Parameters which may be changed to optimize the operation of the sensor may include fiber diameter 922, fiber buffer diameter 924, the inner diameter of the capillary 926, the length of the reaction region (L) 928, the capillary wall thickness 932, the outer diameter of the capillary 934, the diameter if the reduced fiber 936 and the distance between the fiber and the inner wall of the capillary 938. As illustrated in FIG. 7B, a first molecular constituent may be present on both the inner wall of the capillary 950 and the outer wall of the fiber at 920.

Figure 8B:
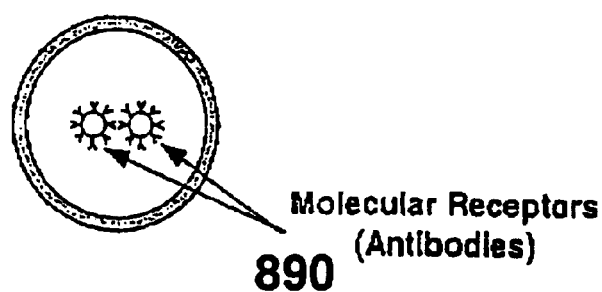
FIG. 8B is a drawing which shows a cross section of a capillary containing two waveguides wherein a molecular receptor is localized on the waveguides.
Figure 8A:
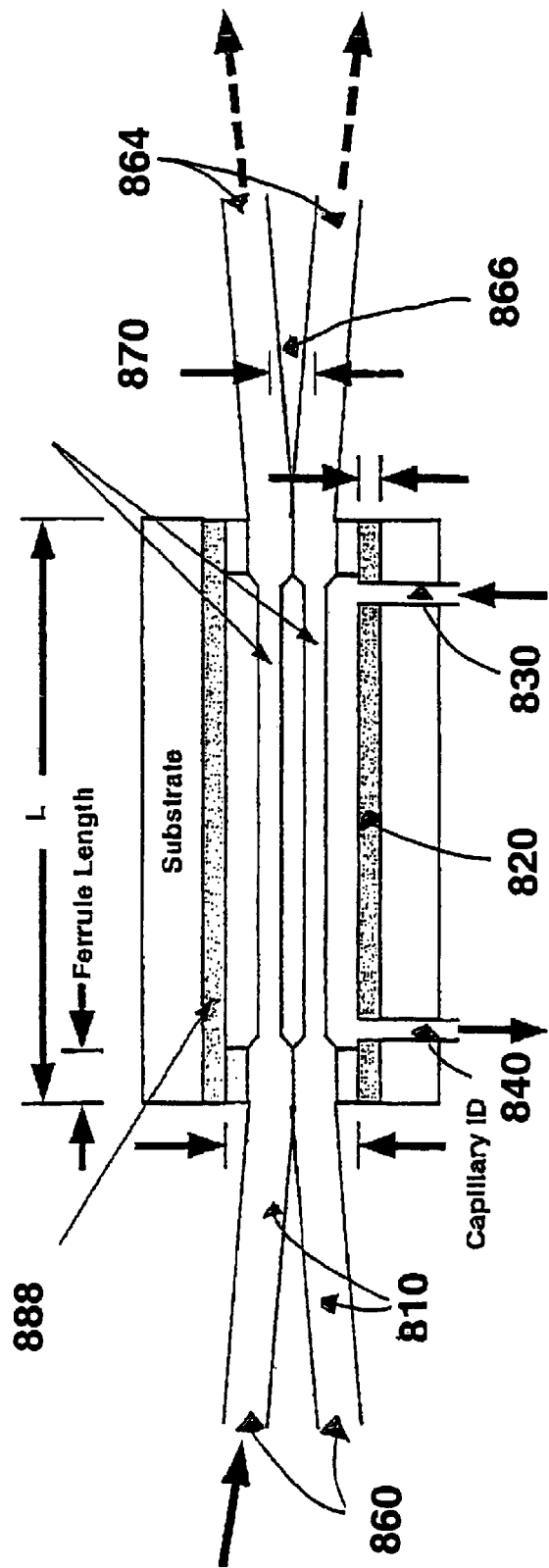
FIG. 8A is a drawing which shows two waveguides in a sample container.

FIG. 8A is a drawing which shows an embodiment of the present invention having two substantially parallel waveguides 810 placed side by side such that the second waveguide is within the evanescent field of the first waveguide at a region along its length. The distance between the two waveguides is potentially adjustable and the center of fiber distance, as illustrated at 866 may vary. The first and second waveguides each have a light-input end 860, a light-output end 864, and a length with an outer surface and a wave-propagating interior. A source of optical energy as from a laser diode is directed into one or both of the light-input ends of the first and second waveguides, such that an evanescent field emanates from one or both of the outer surfaces of the waveguides into the interior of the other. A first optoelectric detector is supported to receive light from the light-output end of the first waveguide and convert the light received into a first electrical signal, and a second optoelectric detector is supported to receive light from the light-output end of the second waveguide and convert the light received into a second electrical signal. A low refractive index isolator 888 is illustrated on the outer wall of the capillary. The drawing illustrates the reduced fiber diameter 870 along a region of the length of the fiber.

In a preferred embodiment, a region of a first waveguide having an attached molecular constituent is situated adjacent a second waveguide, in a sample container. The sample container has a wall with an outer surface and an inner surface, the wall forming a cavity. The container cavity provides sufficient space for the waveguides and a test sample and allows molecular interaction between the constituents. For example, a sample container operative in the present invention is a capillary, illustrated at 820. The sample container has an opening for introduction and withdrawal of a test sample. The illustrated sample container has an opening for the introduction of fluids 830 and an opening for the withdrawal of fluids 840. Optionally, the sample container has multiple openings for introduction and withdrawal of a test sample and other purposes illustratively including, circulation of washing fluids and subsequent reaction components, and insertion of a thermostatic control component.

In FIG. 8B a first molecular constituent is illustrated as present on the outer wall of both waveguides at 890. A first molecular constituent is attached to the first or second waveguide, or both, at least in the region where the second waveguide is within the evanescent field of the first waveguide. A test sample which may contain a second molecular constituent is brought into proximity with a waveguide having an attached first molecular constituent.

Any single mode waveguide which allows emanation of an evanescent field is operative in the optical sensor of the present invention. In a preferred embodiment, two optical fibers are used as waveguides. In a further preferred embodiment, two planar waveguides are used.

A molecular constituent useful in the present invention is characterized by an ability to specifically interact with another molecule, the interaction resulting in a change in an optically detectable property. A molecular constituent is any molecule, or portion of a molecule, that is capable of being attached, directly or indirectly to a waveguide such that it is capable of specific interaction with another molecule present in a test sample. Examples of a molecular constituent illustratively include a protein, a peptide, a polysaccharide, a sugar, an antibody, an antigen, a hapten, a receptor, a ligand such as an agonist or antagonist, a sugar binding protein such as a lectin, a toxin, a virus, a bacterium, a cell, a cell component such as an organelle, a particle such as a liposome, a nucleic acid, a drug and a prion. A molecular constituent further includes fragments or metabolites of the listed substances capable of specific interaction as described. Further, a molecule interacting with another molecule of the present invention is a gas illustratively including NO, $O_2$, $CO_2$. A molecular constituent also illustratively includes a chemical-sensitive polymer, a chemical-sensitive microimprinted polymer and a chemical-sensitive dye.

The terms "interaction" and "binding" are used interchangeably herein and refer to a selective association, through chemical or physical means, of two or more molecules. By "selective association" is meant that a first molecule binds preferentially to a second molecule or with greater affinity than to most other molecules. For example, a DNA molecule will selectively associate with a substantially complementary sequence and not with unrelated nucleic acids.

A test sample containing a molecular constituent to be detected is typically a biological sample. A biological sample is obtained from a human or other animal or from an environmental site where the earth, water or air are to be tested. Environmental sites include outdoor locations as well as indoor location such as laboratories, hospitals and manufacturing facilities. A sample illustratively refers to a cells, tissue or physiological fluid, such as plasma, serum, cerebrospinal fluid, saliva, semen, amniotic fluid, tears, milk, and fluids obtained from respiratory, upper digestive, intestinal, and genitourinary tracts. A test sample also includes fluid or a suspension of solids obtained from wounds, tumors and organs. Further, a test sample is obtained to test for environmental contamination. For example, a surface suspected to be contaminated by bacteria is swabbed and the bacteria obtained are suspended in a solution for later introduction into a biosensor of the present invention.

In one embodiment of the present invention, the interaction of molecular constituents acts to cleave or release molecules attached to the waveguide. For example, a substrate is attached to a waveguide and an enzyme to be detected interacts with the substrate under appropriate conditions. The resulting enzyme activity cleaves the substrate causing a change in an optical property.

In an embodiment of the instant invention, the interaction of molecular constituents results in the formation of another molecular species such that a change in an optical property is detected. For example, an enzyme interacts with a substrate to produce a product deposited on or near the waveguide such that a change in an optical property is detected. Techniques of enzymatic reaction are well known in the art. A preferred example is horseradish peroxidase used in conjunction with diaminobenzidine and $H_2O_2$ or a similar substrate such as tetramethylbenzidine or aminoethylcarbazole.

The term "attached" as used herein to describe the relationship of a first molecular constituent with a waveguide is intended to mean attached either directly or indirectly to the waveguide. An illustrative example of a direct attachment is a link to a pendant moiety on a waveguide via a pendant chemical moiety present on the first molecular constituent. An indirect attachment occurs, for example, where a molecular constituent is optionally attached to a waveguide via a linker. Where a linker is used the choice of linker depends on the surface of the waveguide and the molecular constituent to be attached. Selection of an appropriate combination will be evident to one skilled in the art. For example, where the surface has available Si—OH groups, appropriate linkers include aminoalkyltrialkoxysilanes, aminoalkyltrichlorosilanes, carboxyalkyltrialkoxysilanes, epoxyalkyltrialkoxysilanes, hydroxyalkyltrialkoxysilanes and hydroxyalkyltrichlorosilanes. Further suitable silanes are listed in Silicon Compounds: Register & Review, from United Chemical Technologies, 5th Ed., 1991. Further illustrative examples of linkers include aryl acetylene, diamines, diacids, polyalcohols, polyesters, polyethers, polylysine, polyarginine, polystyrene sulfonate, dextran sulfate, chondroitin, polyacrylic acid, polymethacrylic acid, polyacrylamide, polyallylamine, maleic acid, substituted or unsubstituted polyalkylenes, polyamines, polyamides, polysufonates, polyoxides, polyalkyleneglycols, polystyrenic-based polymers, polyacetals, polysaccharides, polycarbonates, polyurethanes, polyureas, polyamides, polyethyleneimines, polyarylene sulfides, polysiloxanes, polyimides, polyacetates, polymers of monoethylenically unsaturated monomers, polymers of polyvinylidene monomers and mixtures and copolymers of the above polymers. Following linker binding, unreacted functional groups on the waveguide surface are optionally blocked to prevent further reaction.

It will be appreciated by one skilled in the art that a molecular constituent attached to a waveguide is removable according to the mechanism of attachment used. Thus, a wave guide according to the invention is reusable.

An apparatus of the present invention allows detection of a molecular constituent in a test sample where the concentration of the constituent is in the range of $10^{-3}$ M to $10^{-15}$ M or less. Sensitivity of the apparatus will depend in part on the amount and concentration of the constituent attached to the waveguide.

Substances are optionally introduced into the cavity 140 to facilitate an interaction between molecular constituents. For example, a gel is introduced into the cavity. Gels operative in the present invention are any that do not interfere with the desired interaction and illustratively include agarose and acrylamide. The viscosity of a gel is chosen such that a molecular constituent in a sample to be tested remains in the cavity available for interaction with the waveguide attached molecular constituent for an appropriate period of time which is apparent to one of skill in the art.

It will be readily apparent to one of skill in the art that specific interaction between molecular constituents is to some extent dependent on appropriate interaction conditions such as temperature, salt concentration and buffer composition. Solutions used in a biosensor apparatus of the present invention are adjusted according to the desired interaction. An apparatus of the present invention optionally has a thermostatic control for regulating the temperature at which the molecular constituents are brought into contact.

The interaction of molecular constituents causing a change in an optical property is not limited to the interaction of two constituents. Thus, interaction of three or more molecules may be required to cause an optical change. For example, an antibody attached to a waveguide interacts with an antigen to be detected resulting in minimal or undetectable change in an optical property. A third molecular constituent, such as an antibody interacts with the antigen-antibody complex to bring about a change in an optical property.

It should be noted that reference therein to "biomolecular" or "molecular constituent," "binding partner," and so forth are used interchangeably and are not intended to in any way limit the invention, since the invention is applicable to any type of organic/inorganic material, so long as the interaction of one component causes a change in any optical property detectable by the apparatus. Accordingly, the invention is applicable to any chemical/biochemical/bioaffinity/immuno-type interactions of ligands or other types of respective binding partners. Examples include, but are not limited to, antigen-antibody, carbohydrate-lectin, receptor-ligand, binding protein-toxin, substrate-enzyme, effector-enzyme, inhibitor-enzyme, complimentary nucleic acid strands, binding protein-vitamin, binding protein-nucleic acid, reactive dye-protein, and reactive dye-nucleic acid interactions.

As a final note, although the invention assumes the use of glass fibers, polymeric fibers and other materials may be used, depending upon the wavelengths of interest or other aspects of the particular analytical configuration.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. An optical biosensor, comprising:
   a hollow optical waveguide having a light-input end, a light-output end, and a wall with a thickness and an inner surface;
   a second optical waveguide having a light-input end, a light-output end, and a length with an outer surface disposed within the hollow optical waveguide thereby creating a cavity between the inner surface of the hollow optical waveguide and the outer surface of the second optical waveguide;
   a source of optical energy directed into one or both of the light-input ends of the hollow and second optical waveguides, establishing an evanescent field that extends into the cavity from one or both of the inner surface of the hollow optical waveguide and the outer surface of the second optical waveguide;
   a first optoelectric detector operative to receive light from the light-output end of the hollow optical waveguide and convert the light received into a first electrical signal;
   a second optoelectric detector operative to receive light from the light-output end of the second optical waveguide and convert the light received into a second electrical signal;
   a first biomolecular constituent attached to one or both of the inner wall of the hollow optical waveguide and the outer surface of the second optical waveguide, such that the first biomolecular binding partner is substantially within the evanescent field, if present; and
   a fluid within the cavity which may contain a second biomolecular constituent, the second constituent having a binding affinity to the first biomolecular constituent, such that if binding occurs between the biomolecular constituents, a representative change occurs in the light emerging from one or both of the output ends of the hollow and second optical waveguides and the electrical signals from the optoelectric detectors.

2. The optical biosensor of claim 1, wherein the hollow optical waveguide is a capillary, and the second optical waveguide is an optical fiber.

3. The optical biosensor of claim 1, wherein;
   the light conducted by one or both of the waveguides assume different optical polarities; and
   at least the second optical detector is able to sense a change in the optical polarity.

4. The optical biosensor of claim 1, wherein;
   the light conducted by the hollow optical waveguide is able to propagate in multiple optical modes; and
   the presence or absence of the binding determines the rate of propagation.

5. The optical biosensor of claim 1, wherein the second optoelectric detector includes an aperture through which the second optical waveguide protrudes to minimize interference between the energy received by the first and second optoelectric detectors.

6. The optical biosensor of claim 1, wherein the second waveguide is sealed within the hollow waveguide, thereby creating the cavity.

7. The optical biosensor of claim 1, including a plurality of hollow and second optical waveguides, each having a cavity in common fluid communication.

8. The optical biosensor of claim 1, wherein the electrical signals from the first and second optoelectric detectors are compared as part of the analysis.

9. The optical biosensor of claim 1, wherein the biomolecular constituents include the following:
   antigen-antibody,
   substrate-enzyme,
   effector-enzyme,
   inhibitor-enzyme,
   complimentary nucleic acid strands,
   binding protein-vitamin,
   binding protein-nucleic acid,
   reactive dye-protein, and
   reactive dye-nucleic acid interactions.

10. An optical biosensor, comprising:
    a hollow capillary having a light-input end, a light-output end, and a wall with a thickness and an inner surface;
    an optical fiber having a light-input end, a light-output end, and a length with an outer surface disposed within the capillary, thereby creating a cavity between the inner surface of the capillary and the outer surface of the fiber;
    a source of optical energy directed into one or both of the light-input ends of the capillary and fiber, such that an evanescent field extends into the cavity from one or both of the inner surface of the capillary and the outer surface of the fiber;
    a first optoelectric detector operative to receive light from the light-output end of the capillary and convert the light received into a first electrical signal;
    a second optoelectric detector operative to receive light from the light-output end of the fiber and convert the light received into a second electrical signal;
    a first biomolecular constituent attached to one or both of the inner wall of the hollow optical waveguide and the outer surface of the second optical waveguide such that the first biomolecular binding partner is substantially within the evanescent field if present; and
    a fluid within the cavity which may contain a second biomolecular constituent, the second constituent having a binding affinity to the first biomolecular constituent, such that if binding occurs between the biomolecular constituents, a representative change occurs in the light emerging from one or both of the output ends of the hollow and second optical waveguides and the electrical signals from the optoelectric detectors.

11. The optical biosensor of claim 10, wherein;
    the light conducted by one or both of the capillary and optical fiber assume different optical polarities; and
    at least the second optical detector is able to sense a change in the optical polarity.

12. The optical biosensor of claim 10, wherein;
    the light conducted by the capillary is able to propagate in multiple optical modes; and
    the presence or absence of the binding determines the propagational mode.

13. The optical biosensor of claim 10, wherein the second optoelectric detector includes an aperture through which the optical fiber protrudes to minimize interference between the energy received by the first and second optoelectric detectors.

14. The optical biosensor of claim 10, wherein the optical fiber is sealed within the capillary using ferrules, thereby creating the cavity.

15. The optical biosensor of claim 10, including a plurality of hollow and second optical waveguides, each having a cavity in common fluid communication.

16. The optical biosensor of claim 1, wherein the electrical signals from the first and second optoelectric detectors are compared as part of the analysis.

17. The optical biosensor of claim 1, wherein the biomolecular constituents include the following:
- antigen-antibody,
- substrate-enzyme,
- effector-enzyme,
- inhibitor-enzyme,
- complimentary nucleic acid strands,
- binding protein-vitamin,
- binding protein-nucleic acid,
- reactive dye-protein, and
- reactive dye-nucleic acid interactions.

* * * * *